United States Patent [19]

Meyer

[11] 4,178,638

[45] Dec. 18, 1979

[54] SPLIT LEAFLET CHECK VALVES

[75] Inventor: Louis C. Meyer, Denver, Colo.

[73] Assignees: Louis C. Meyer, Denver; Anna T. Loeffler, Englewood, both of Colo.

[21] Appl. No.: 820,769

[22] Filed: Aug. 1, 1977

[51] Int. Cl.² .......................... A61F 1/22; F16K 15/03
[52] U.S. Cl. .......................................... 3/1.5; 137/512; 137/527; 251/212
[58] Field of Search ................... 3/1.5; 137/512, 527, 137/527.2, 527.8; 251/212

[56] References Cited

U.S. PATENT DOCUMENTS

| 116,605 | 7/1871 | Lewis | 137/527 |
|---|---|---|---|
| 2,911,997 | 11/1959 | Schramm | 251/212 X |
| 2,956,582 | 10/1960 | Pranter | 137/527 X |
| 3,127,148 | 3/1964 | Collar | 137/527 X |
| 3,589,392 | 6/1971 | Meyer | 3/1.5 X |
| 4,034,780 | 7/1977 | Horvath | 137/527 X |

FOREIGN PATENT DOCUMENTS 9095 of 1879 Fed. Rep. of Germany ............ 137/527
4347 of 1913 United Kingdom ...................... 137/527

Primary Examiner—Robert G. Nilson
Attorney, Agent, or Firm—Frank C. Lowe

[57] ABSTRACT

The invention concerns improvements in a split leaflet check valve. A pair of curved leaflets are hinged to a base ring for swinging movement from a normally closed position to an open position whenever a fluid is moving through the conduit wherein the valve is mounted. At the closed position, portions of each leaflet are seated upon the base ring and other portions are seated against each other to effect the closure. At the open position the leaflets, curved to the curvature of the conduit, lie against the sides of the passageway to provide for flow of fluid through the check valve with a minimum of turbulence. The hinge at the base of each leaflet is formed as a hook reaching into a side socket in the outer wall of the base ring. This check valve may be used where a minimal flow turbulence is desired such as in pipeline systems pumping sludge, artificial heart pumps and cardiac surgery.

5 Claims, 8 Drawing Figures

U.S. Patent Dec. 18, 1979 Sheet 1 of 2 4,178,638
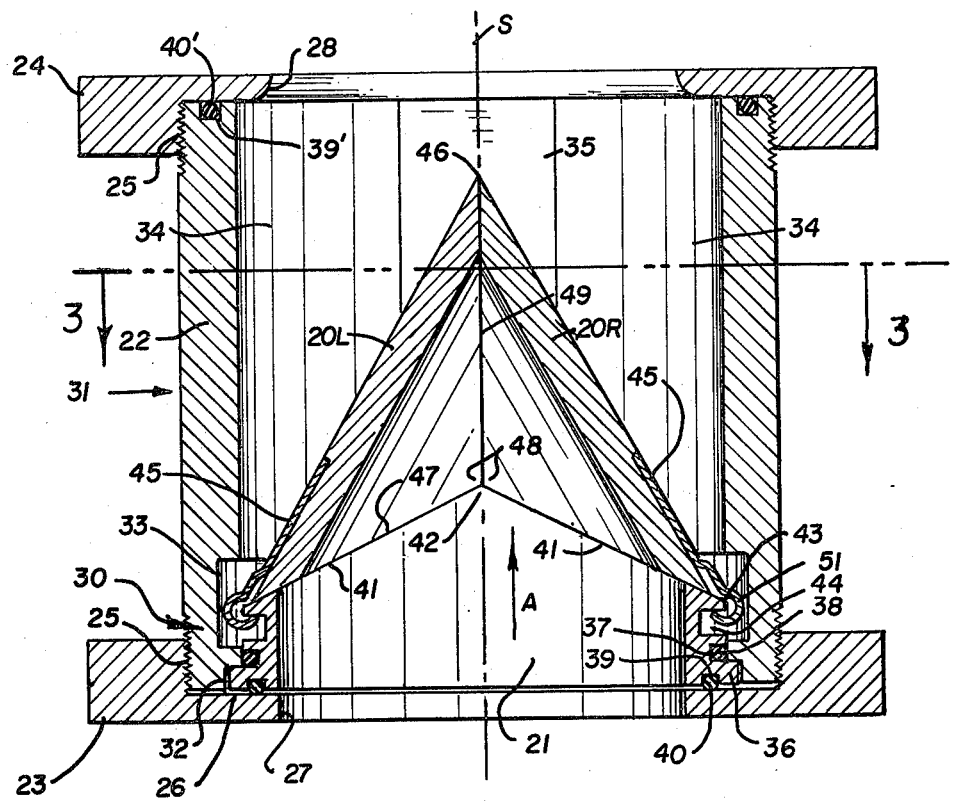
Fig. 1
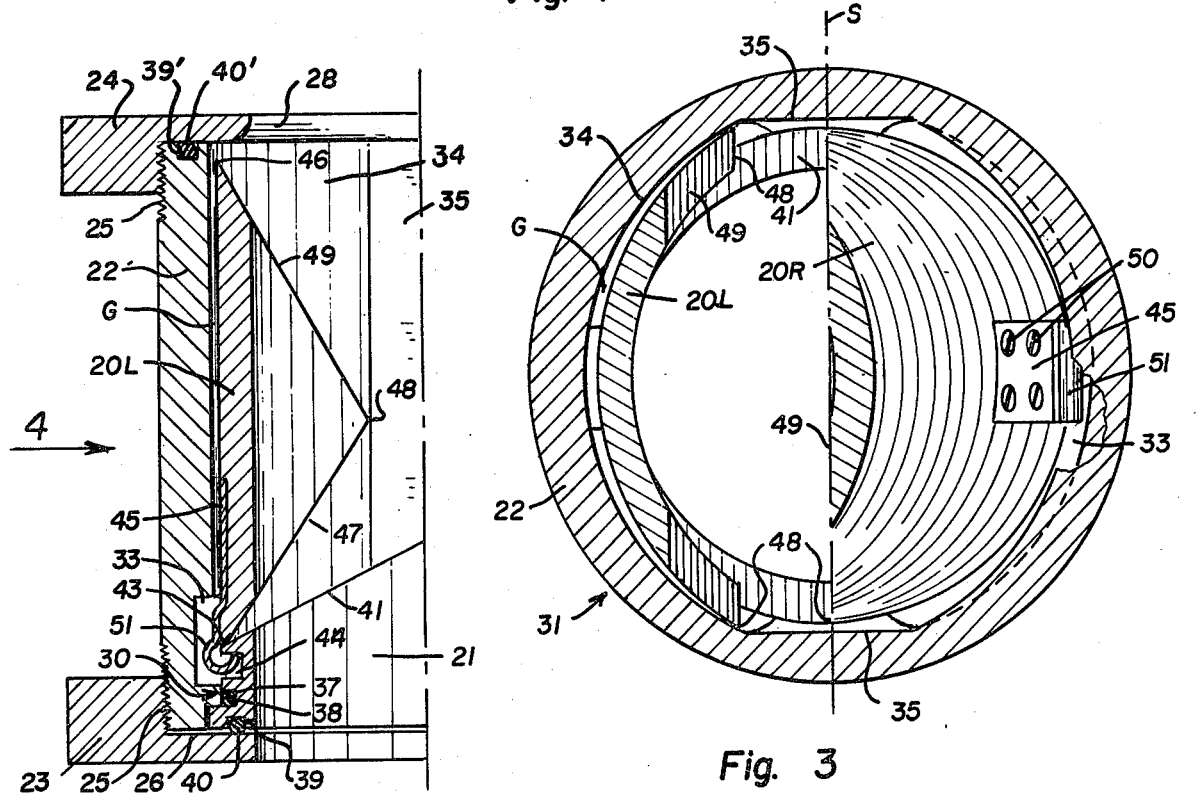
Fig. 2
Fig. 3

SPLIT LEAFLET CHECK VALVES

This invention relates to improvements in check valves of the type disclosed in my U.S. Pat., No. 3,589,392, and which is sometimes called a "split leaflet check valve". The invention will be herein referred to as a "leaflet valve" or a "leaflet check valve".

The leaflet valve disclosed in my prior patent was developed to provide a check valve for cardiac surgery. A hollow ring-shaped body supports a pair of opposing, curved leaflets hinged at the body for swinging movement from a closed position when the leaflets are together and seated upon the body to an open position when the leaflets move apart to opposite sides of the body with the curvature thereof providing an unobstructed passageway through the body. This leaflet valve is adapted to be placed in a tubular passageway such as an artery comparable in diameter to the ring-shaped body with the result that the flow through the passageway in one direction is unobstructed, with a minimum of turbulence when the valve is open. Flow in the other direction effects a prompt closure of the valve.

In the prior patent, each curved leaflet is made of a synthetic resin plastic and is integral with the body. It is connected thereto at the hinge portion which is capable of repeated hinging and flexing through many cycles of operation. As the unit was tested, its performance was so good that other uses for the valve became apparent, but a better mode of hinging the leaflets to the body was needed, especially where the valve was to be made of a different material, such as metal.

The present invention was conceived and developed with the above considerations in view and the invention comprises, in essence, a mechanical hinging arrangement to secure each leaflet to the body, which includes a base ring in a retainer tube, to permit the leaflets to function in an effective manner.

An object of the invention is to provide a novel and improved leaflet valve wherein the leaflets are hinged to the body of the valve in a loosely swinging manner whereby seating of the leaflets upon the body to close the valve is in a natural, self-aligning manner.

Another object of the invention is to provide a novel and improved leaflet valve with a mechanical hinging arrangement of the leaflets upon the body of the valve capable of operation over a long period of time with no significant wear and in a manner which completely eliminates material fatigue problems.

Another object of the invention is to provide a novel and improved leaflet check valve which can effectively operate in fluids which are viscous, such as slurries and sludges, with a comparatively free action and with the leaflets capable of yielding in their positions whenever obstructed by sludge substances.

Another object of the invention is to provide a novel and improved leaflet check valve which may also function as a check valve in heart pumps and for cardiac surgery, and which is simple, economical and reliable in its operation.

With the foregoing and other objects in view, my present invention comprises certain constructions, combinations and arrangements of parts and elements as hereinafter described, defined in the appended claims, and illustrated in preferred embodiment by the accompanying drawing in which:

FIG. 1 is a longitudinal sectional view of the improved leaf valve showing the leaves closed.

FIG. 2 is a fragmentary sectional view the same as a portion of FIG. 1, but with a leaf being open.

FIG. 3 is a transverse sectional view as taken from the indicated line 3—3 at FIG. 1, but with one leaf open.

Figure 4:
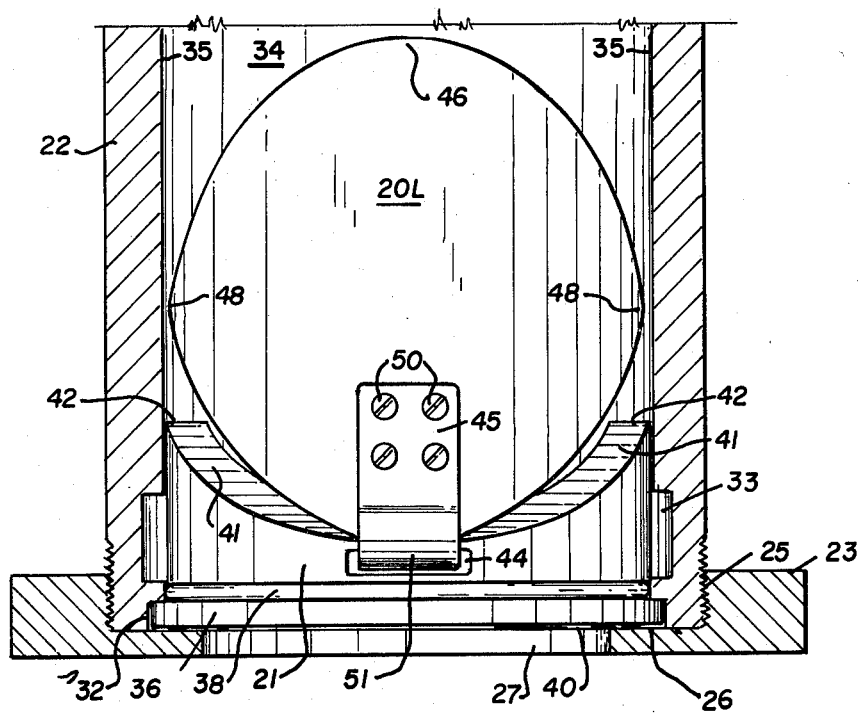
FIG. 4 is a longitudinal view from the indicated arrow 4 at FIG. 2, with the outer shell broken away and in section to show the leaf and its base in full.

Referring more particularly to the drawings, the improved leaflet check valve consists, basically, of four components, namely, two leaflets, a base ring to carry and seat these leaflets and a retainer tube to hold the leaflets together and to connect the valve into a conduit. The arrangement shown at FIGS. 1 to 4 is an embodiment especially useful as a general purpose check valve suitable for controlling the flow of sludge and similar liquids which can easily clog a conventional valve in a conduit. Two opposing curved leaflets 20R and 20L are seated and are hinged upon a base ring 21, as will be described. A retainer tube 22 embraces the base ring and the leaflets. This retainer tube 22 may be considered as a short portion of a pipeline wherein the valve is located and each end of the retainer tube is adapted to be connected to the pipeline in any conventional manner. In the drawing, an intake flange 23 and a discharge flange 24 are connected to their respective ends of the retainer tube as by threads 25 as illustrated. The flanges connect to mating flanges in the pipeline, which are not shown because they are conventional.

The base ring 21 holds the leaflets in place by hinge means hereinafter described and permits the leaflets to open and close within the tube 22. This valve is essentially of mirror symmetry from each side of a longitudinal central plane as indicated in edge view as "S" at FIGS. 1 and 3. Thus, simultaneous movement of the leaflets 20R and 20L away from and towards this plane of symmetry S opens and closes the valve. A normal flow through the valve, from the intake end to the discharge end, as in the direction of the indicated arrow A at FIG. 1, opens the leaflets and a reverse flow will close them. In opening, the leaflets 20R and 20L are adapted to swing against the side walls of the retainer tube 22 and these curved leaflets lie close to the curved side walls of the retainer tube to provide a full, uninterrupted passageway through the valve when so opened.

Each flange 23 and 24 is fitted upon the retainer tube 24 as by threads 25 and includes an internal, rabbeted step with the thread 25 forming the circular wall of this step. The floor portion 26 of each step extends inwardly to define a circular, square-cut passage wall 27 at the intake flange 23 and a circular, bellmouthed passageway 28 at the discharge flange 24. The passage wall 27 and the passageway 28 define the passage diameter through the valve and as such, they will normally have the same diameter as the internal diameter of the conduit or pipe to which the valve will be connected. The floor portion 26 of this square-cut passage wall 27 of the intake flange 23 is adapted to hold the base ring 21 in place as will be described. The bellmouth passageway 28 of the discharge flange 24 is formed to reduce flow turbulence caused by the necessary enlarging of the passageway through the tube 22 to accommodate the leaflets 20R and 20L when they are opened with the leaflets being positioned close to the retainer tube walls and out of the passage defined by the flanges.

The retainer tube has a length sufficient to effectively house both the base ring 21 and the leaflets 20R and 20L. A circular base holding section 30 is located adjacent to the intake flange 23. The leaf holding section 31 beyond the base holding section 30 is more nearly oval when the tube is viewed in section as shown at FIG. 3. The inner wall of the circular base holding section 30 includes an inset, rabbeted shoulder 32 at the end of the tube and a circular slot 33 beyond this seat to provide space for the leaf hinges. The inner wall of the oval leaf holding section 31 includes diametrically opposing cylindrical segments 34 which are formed at a curvature approximating the curvature of the leaflets 20R and 20L. These segment surfaces 34 are spaced apart from opposite sides of the plane of symmetry S a distance sufficient to permit these leaflets to lie close to this inner wall when the leaflets are open. This inner wall also includes diametrically opposing flats 35 centered at the plane of symmetry S and spaced to loosely engage the side corners of the leaflets to facilitate guiding these leaflets upon the base ring seat as will be described.

The base ring 21 is a circular member having an internal diameter the same as the passage wall diameter 27 defining the passage through the valve and an outside diameter slightly less than the diameter of the base holding section 30 for a free sliding fit thereinto. A flange 36 at the base of this ring 21 fits into the retainer tube slot 33 and the base ring 21 is held in place by the floor 26 of the rabbeted step of the intake flange 23. A circumferential slot 37 in the ring 21 carries an O-ring 38 to seal the base ring against the base holding section 30. An end slot 39 in the base ring carries an O-ring 40 to seal the base ring against the shoulder 36. It is to be noted that a slot 39' carrying O-ring 40' may be provided at the discharge flange 24 to seal that flange connection.

The top of the base ring 21 is formed with two beveled seating surfaces 41 at a selected inclination which is preferably approximately 54° from the plane of symmetry S. This seat thus slopes from an apex point 42 at the plane of symmetry and from each side thereof to diametrically opposite edge points 43 where the leaf hinges are located. To complete the base ring, hinge sockets 44 are located below each edge point 43 and it is to be noted that these hinge sockets 44 are located at the circular slot 33 to provide clearance for the hinges connecting the leaflets 20R and 20L to the base ring 21.

The leaflets 20R and 20L are cylindrical segments having their edges forming a quadrilateral and each is symmetrical from each side of a central cylindrical element which extends from the hinge 45 at the base of the leaflet to a top point 46 at the plane of symmetry A when the leaflet is at its closed position. When at the closed position, this central cylindrical element is inclined about 30° from the plane of symmetry to establish the geometrical configuration of the leaflet when upon the seat 41 of the base ring. The triangular portion at each side of each leaflet includes a base edge 47 extending from each side of the central element at the hinge 45 to a side corner 48 and this base element is proportioned and shaped to fit the seat surface 41 of the base ring with the side corner 48 being at the apex 42. When so fitted, the closing edge 49 at each side of the leaflet will extend from the side corner 48 at the apex 42 and upwardly on the plane of symmetry S to the top point 46. Accordingly, this closing edge 49 of each leaflet will engage the opposing closing edge 49 of the opposing leaflet to close the valve when at the position best shown at FIG. 1.

In the embodiment shown at FIGS. 1-4, the walls of the leaflets 20R and 20L, the base ring 21 and the retainer tube 22 are illustrated as being comparatively thick and as such, the check valve may be made of metal, as by casting, and even made of selected, rigid types of synthetic resin plastics. If made of metal, or even selected plastics, the thick wall leaflets 20R and 20L may be hollow, or laminated in such a manner as to reduce their weight.

With this thick wall arrangement, the hinges 45 are preferably metal strips embedded in and secured to their respective leaflets as by lock screws 50. (It is to be noted that in other embodiments hereinafter described, the hinges may be also integral with the leaflets.) Each hinge 45 is a strap of suitable width to provide for good line contact in the hinge socket 44 of the base ring and the portion of the hinge extending below the base of the leaflet is a cylindrically curved hook 51 to underlie the edge point 43 of the ring seat 41 and reach into the socket 44. The edge of the hook 51 engages the upper surface of the socket 44 that is, a flat surface opposite to the seat surface 41 and the pivoting action of this hinge 51 by this line engagement upon a surface, permits a comparatively free swinging movement of the leaflet from the closed to the open positions as indicated at FIGS. 1 and 2.

It is to be noted that the angles selected for the seat surface 41 and the edges of the leaflets 20R and 20L are such that whenever the valve closes and the leaflets are seated, they will, responsive to fluid pressure against them, shift to a balanced closed seating position as best illustrated at FIG. 1. If a slight misalignment occurs when the valve closes, the leaflets will naturally align themselves to the desired balanced position. Thus, a precise hinging action is unnecessary and it was found that a loosely fitted hinge such as illustrated, was far more preferable than a precisely-fitted, pivoted hinge. If the hinge was mounted upon a pintle or the like, perfect sealing could not be attained. It was also found that when the leaflets opened as shown at FIGS. 2 and 3, a small gap G between each leaflet and the wall of the retainer tube 22 was desirable to prevent a vacuum from forming behind each leaflet when the flow through the valve was reversed which would prevent the leaflets from closing. Accordingly, this small gap G ensures a quick closure of the check valve whenever the direction of flow reverses.

Figure 5:
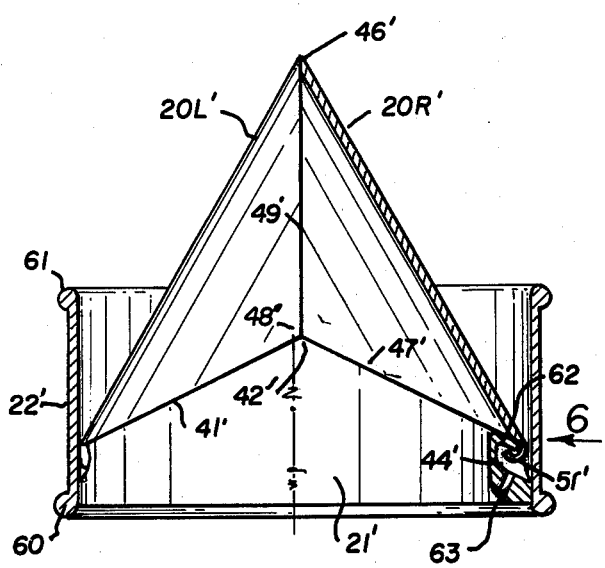
FIG. 5 is a longitudinal view, partly in section and similar to FIG. 1, but showing a modified construction thereof such as may be used as a heart valve.
Figure 6:
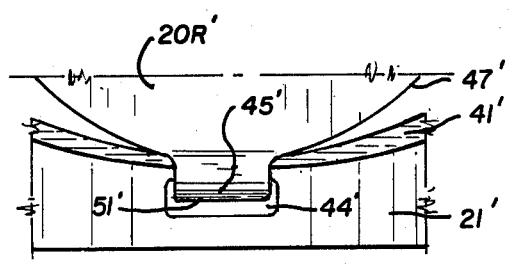
FIG. 6 is a fragmentary view of a leaf hinge as taken from the indicated arrow 6 at FIG. 5, but with the leaf being in an open position.
Figure 7:
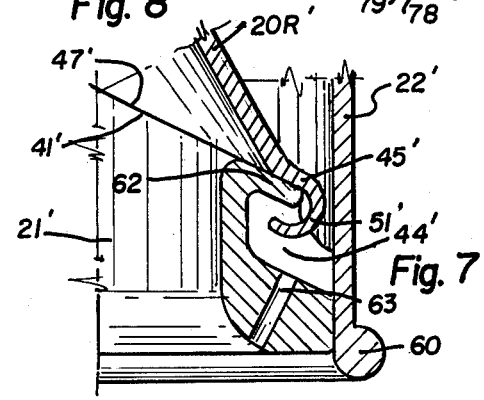
FIG. 7 is a fragmentary sectional view of a portion of the showing at FIG. 5, but on an enlarged scale.

The modified structure shown at FIGS. 5–7 is a unit adapted for an artificial heart or other delicate apparatus where a direct flow through the valve must be with minimal turbulence and a reverse flow must be checked almost instantly. The leaflets 20'R and 20'L are comparatively thinwalled units and the hinge 45' at the base of each leaflet is integral with the leaflet. The base ring 21' is essentially the same structure as heretofore described, but the hinge sockets 44' are inset a short distance to permit the hinge 45' to be carried in this socket without the need for a circular clearance slot in the retainer tube 22', such as the slot 33 heretofore described. The retainer tube 22' is also modified to be a short thinwalled tubular member with beads 60 and 61 at the edges, instead of flanges as heretofore described (although other conduit connective means may be used). Each hinge socket 44' illustrated in this embodiment provides for a downsloped lip 62 to engage the hook 51' of the hinge whenever the leaflet swings to the open position.

The base ring 21' is secured in place by a press fit into the retainer tube 22' with the leaflets 20' being in place. Thus, the need for O-rings to effect sealing in this construction is eliminated. Since this valve is for a heart valve, it is necessary to prevent any blood stagnation and clotting in the hinge sockets 44'. Thus, a weep hole 63 is provided in the base ring 21' on each socket 44' to connect the socket with the inside of the ring. Each time the valve closes a small amount of blood will leak from the hinge socket 44' to the interior of the valve.

Figure 8:
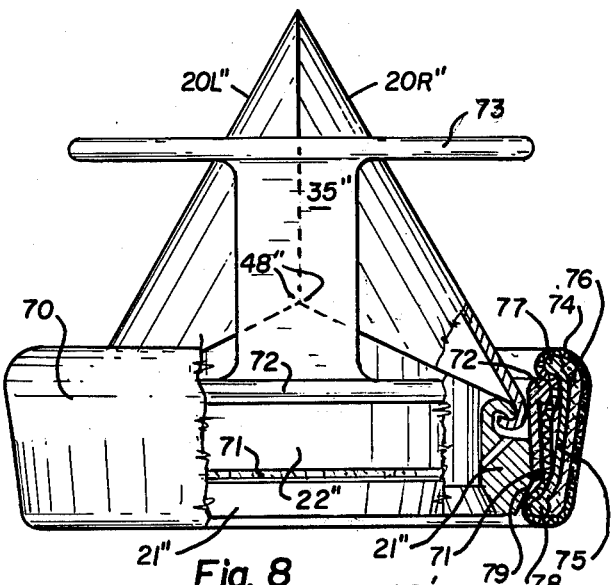
FIG. 8 is an elevational view of another modified form of valve such as may be used in heart surgery with portions broken away to show parts otherwise hidden from view.

The construction shown at FIG. 8 illustrates a further modified leaflet check valve which is adapted for cardiac surgery. The leaflets 20"R and 20"L and the base ring 21" are essentially the same as shown at FIG. 5 and heretofore described. The retainer tube 22" is modified and narrowed to hold a suture ring 70 to permit the valve to be secured in an artery or vein associated with cardiac surgery. This retainer tube 22" fits upon the base ring 21" with a snug, press fit and with the lower edge of the ring being secured to the base ring as by a solder bead 71. The upper edge of this retainer tube extends only a short distance above the hinge sockets 44 and is formed with an outward bead 72. An extension of this retainer tube above the base ring includes a pair of diametrically opposed flats 35" to engage the side corners 48"0 of the leaflets, shown in broken lines at FIG. 8, as they swing from a closed to an open position. A stabilizer ring 73 at the top of these flats completes the unit.

The structure of the suture ring 60 must be such as to permit it to receive suture threads and the outer layer 74 of the ring is a suture cloth of suitable synthetic resin fibers such, for example, as woven polyester. The cloth layer 74 is wrapped about a lock ring 75 in any suitable manner with padding 76 at the outer face to facilitate sewing suture thread into the ring. The padding may be of any suitable fibrous or soft resilient material or it may be formed by several wraps of the suture cloth 74 forming the outer surface of the ring 70.

The lock ring 75 is formed with beads 77 and 78 at the top and bottom and is inwardly arched to snugly embrace the retainer tube 22', the beads being turned inwardly from the rim and proportioned in such a manner as to require a substantial pressure to snap the suture ring onto the retainer tube to prevent its removal. It is to be noted that the lower corner of the base ring may be beveled as at 79 to better receive and hold the lower bead 78 of the suture ring.

I have now described my invention in considerable detail. However, it is obvious that others skilled in the art can build and devise alternate and equivalent constructions which are nevertheless within the spirit and scope of my invention. Hence, I desire that my protection be limited not by the constructions illustrated and described, but only by the proper scope of the appended claims.

What I claim is:

1. A split leaflet check valve comprising:
   (a) a base ring having a seat surface at one side thereof and a plurality of underhanging socket portions at the outer wall thereof with a flat undersurface of each socket being opposite to the seat surface;
   (b) a like plurality of curved leaflets with each having a base edge and side edges extending to a top point proportioned such that with the valve closed each leaflet base edge seats on the base ring seat surface and each leaflet side edge seats against an adjacent side edge of an adjacent leaflet; and
   (c) a hinge arm extended from the base edge of each leaflet and to a socket portion at the base ring to attach the leaflet to the base ring, and wherein each hinge terminates as a cylindrically curved hook extending into said socket portion with the linear edge of the hook bearing against the aforesaid undersurface of the socket whenever leaflets are moved to an open position by flow of fluid through the valve.

2. A split leaflet check valve comprising:
   (a) a base ring having a seat surface at one side thereof and socket portions at the outer wall thereof;
   (b) a plurality of curved leaflets with each having a base edge, side edges extending to a top point and a hinge means extending from the base edge and to a socket portion of the base ring to attach the leaflet to the base edge, and with each leaflet being proportioned such that with the valve closed each leaflet base edge seats on the base ring seat surface and each leaflet side edge seats against an adjacent side edge of an adjacent leaflet; and
   (c) a retainer tube wherein said base ring is fitted with said leaflets moving against the retainer tube when they swing to an open position, and with said retainer tube being ovate in section at the portion adjacent to each leaflet to receive the leaflets when they open and thereby provide a maximum passageway clearance when the valve is open.

3. A split leaflet check valve comprising:
   (a) a base ring having a seat surface at one side thereof and diametrically opposing socket portions at the outer wall thereof;
   (b) a pair of diametrically opposed curved leaflets with each having a base edge, side edges extending to a top point and a hinge means extending from the base edge and to a socket portion of the base ring to attach the leaflet to the base edge, and with each leaflet being proportioned such that with the valve closed, each leaflet base edge seats on the base ring seat surface and each leaflet side edge seats against an adjacent side edge of an adjacent leaflet;
   (c) a retainer tube wherein said base ring is fitted with said leaflets moving against the retainer tube when they swing to an open position; and
   (d) a flat surface on the retainer tube at the side of each leaflet to engage the adjacent leaflet point between the base edge and side edge of the leaflet as the leaflet swings from the open to the closed position and thereby limit lateral shifting of the leaflet during its opening and closing movements.

4. The check valve defined in claim 3, wherein:
   (a) the retainer tube is a comparatively narrow member embracing the base ring; and
   (b) the flat surfaces are formed as straplike members extended above the retainer tube.

5. The check valve defined in claim 3, wherein:
   the retainer tube is a comparatively narrow member; and
   a suture ring is mounted thereon.

* * * * *